United States Patent
Nagamatsu et al.

(10) Patent No.: US 9,913,782 B2
(45) Date of Patent: Mar. 13, 2018

(54) COMPOSITION CONTAINING COMPOSITE PARTICLES FOR SCREENING OUT UV RADIATION, WITH A MEAN SIZE OF GREATER THAN 0.1 ÂµM, AND HYDROPHOBIC SILICA AEROGEL PARTICLES

(71) Applicant: L'OREAL, Paris (FR)

(72) Inventors: Yasuko Nagamatsu, Tokyo (JP); Maud Willien, Vitry-sur-Seine (FR); Didier Candau, Bievres (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/781,427

(22) PCT Filed: Mar. 20, 2014

(86) PCT No.: PCT/EP2014/055586
§ 371 (c)(1),
(2) Date: Sep. 30, 2015

(87) PCT Pub. No.: WO2014/161722
PCT Pub. Date: Oct. 9, 2014

(65) Prior Publication Data
US 2016/0030304 A1    Feb. 4, 2016

(30) Foreign Application Priority Data
Apr. 5, 2013   (FR) ...................................... 13 53067

(51) Int. Cl.
| A61K 8/25 | (2006.01) |
|---|---|
| A61K 8/42 | (2006.01) |
| A61K 8/29 | (2006.01) |
| A61Q 19/00 | (2006.01) |
| A61Q 19/08 | (2006.01) |
| A61K 8/02 | (2006.01) |
| A61Q 17/04 | (2006.01) |
| A61K 8/81 | (2006.01) |
| A61K 8/04 | (2006.01) |
| A61K 8/31 | (2006.01) |
| A61K 8/34 | (2006.01) |
| A61K 8/35 | (2006.01) |
| A61K 8/37 | (2006.01) |
| A61K 8/40 | (2006.01) |
| A61K 8/41 | (2006.01) |
| A61K 8/46 | (2006.01) |
| A61K 8/49 | (2006.01) |
| A61K 8/55 | (2006.01) |
| A61K 8/58 | (2006.01) |
| A61K 8/73 | (2006.01) |
| A61K 8/84 | (2006.01) |
| A61K 8/86 | (2006.01) |
| A61K 8/894 | (2006.01) |
| A61K 8/92 | (2006.01) |
| A61Q 1/00 | (2006.01) |

(52) U.S. Cl.
CPC ............ *A61K 8/0283* (2013.01); *A61K 8/025* (2013.01); *A61K 8/0241* (2013.01); *A61K 8/0279* (2013.01); *A61K 8/042* (2013.01); *A61K 8/25* (2013.01); *A61K 8/29* (2013.01); *A61K 8/31* (2013.01); *A61K 8/345* (2013.01); *A61K 8/35* (2013.01); *A61K 8/37* (2013.01); *A61K 8/40* (2013.01); *A61K 8/41* (2013.01); *A61K 8/466* (2013.01); *A61K 8/4966* (2013.01); *A61K 8/55* (2013.01); *A61K 8/585* (2013.01); *A61K 8/73* (2013.01); *A61K 8/8152* (2013.01); *A61K 8/84* (2013.01); *A61K 8/86* (2013.01); *A61K 8/894* (2013.01); *A61K 8/92* (2013.01); *A61Q 1/00* (2013.01); *A61Q 17/04* (2013.01); *A61Q 19/00* (2013.01); *A61Q 19/08* (2013.01); *A61K 2800/412* (2013.01); *A61K 2800/592* (2013.01); *A61K 2800/594* (2013.01); *A61K 2800/621* (2013.01); *A61K 2800/654* (2013.01)

(58) Field of Classification Search
CPC .......... A61Q 1/02; A61Q 19/08; A61Q 15/00; A61Q 19/001; A61Q 1/04; A61Q 1/10; A61Q 11/00; A61Q 17/04; A61Q 19/00; A61Q 19/004; A61Q 19/008; A61Q 19/02; A61Q 19/04; A61Q 1/00; A61Q 1/06
See application file for complete search history.

(56) References Cited

U.S. PATENT DOCUMENTS

2004/0105829 A1* 6/2004 Chuah .................... A61K 8/044
424/68
2005/0255134 A1* 11/2005 Hasenzahl ............... A61K 8/25
424/401
(Continued)

FOREIGN PATENT DOCUMENTS

FR              2 968 979 A1    6/2012
WO     WO-2013/190136 A2    12/2013

*Primary Examiner* — Audrea Buckley
(74) *Attorney, Agent, or Firm* — Polsinelli PC

(57) ABSTRACT

The present invention relates to a composition comprising, in a cosmetically acceptable medium: a) composite particles with a mean size of greater than 0.1 µm, containing a matrix comprising i) at least one organic material and/or at least one mineral material and ii) at least titanium dioxide; and b) hydrophobic silica aerogel particles. The invention also relates to a cosmetic process for caring for and/or making up human keratin materials, especially bodily or facial skin or the hair, comprising at least the application, to the surface of the keratin material, of a composition as defined previously. The invention also relates to a non-therapeutic cosmetic process for limiting the darkening of the skin and/or improving the color and/or uniformity of the complexion, comprising the application, to the surface of the keratin material, of a composition as defined previously. The invention also relates to a non-therapeutic cosmetic process for preventing and/or treating the signs of ageing of a keratin material, comprising the application, to the surface of the keratin material, of a composition as defined previously.

20 Claims, No Drawings

(56) References Cited

U.S. PATENT DOCUMENTS

| | | | |
|---|---|---|---|
| 2009/0186055 A1* | 7/2009 | Dumousseaux | A61K 8/11 424/401 |
| 2009/0237648 A1* | 9/2009 | Armstrong | G01N 21/65 356/72 |
| 2009/0247648 A1* | 10/2009 | Zhao | A61K 8/585 514/772 |
| 2010/0203118 A1* | 8/2010 | Tanaka | A61K 8/11 424/451 |
| 2011/0195100 A1 | 8/2011 | Bruning et al. | |

* cited by examiner

COMPOSITION CONTAINING COMPOSITE PARTICLES FOR SCREENING OUT UV RADIATION, WITH A MEAN SIZE OF GREATER THAN 0.1 ÂµM, AND HYDROPHOBIC SILICA AEROGEL PARTICLES

CROSS REFERENCE TO RELATED APPLICATIONS

This application is a National Phase filing under 35 U.S.C. §371 of PCT/EP2014/055586 filed on Mar. 20, 2014; and this application claims priority to Application No. 1353067 filed in France on Apr. 5, 2013. The entire contents of each application are hereby incorporated by reference.

The present invention relates to a composition comprising, in a cosmetically acceptable medium:
- a) at least composite particles with a mean size of greater than 0.1 µm, containing
  - i) a matrix consisting of at least one organic material and/or at least one mineral material and
  - ii) at least titanium dioxide, optionally treated with a surface agent; and
- b) hydrophobic silica aerogel particles.

The invention also relates to a cosmetic process for caring for and/or making up human keratin materials, especially bodily or facial skin or the hair, comprising at least the application, to the surface of the keratin material, of a composition as defined previously.

The invention also relates to a non-therapeutic cosmetic process for limiting the darkening of the skin and/or improving the colour and/or uniformity of the complexion, comprising the application, to the surface of the keratin material, of a composition as defined previously.

The invention also relates to a non-therapeutic cosmetic process for preventing and/or treating the signs of ageing of a keratin material, comprising the application, to the surface of the keratin material, of a composition as defined previously.

It is known that UV radiation with wavelengths of between 280 nm and 400 nm permits tanning of the human epidermis and that radiation with wavelengths between 280 and 320 nm, known as UV-B rays, harms the development of a natural tan. Exposure is also liable to bring about a detrimental change in the biomechanical properties of the epidermis, which is reflected by the appearance of wrinkles, leading to premature ageing of the skin.

It is also known that UV-A rays with wavelengths of between 320 and 400 nm penetrate more deeply into the skin than UV-B rays. UV-A rays cause immediate and persistent browning of the skin. Daily exposure to UV-A rays, even of short duration, under normal conditions can result in damage to the collagen fibres and the elastin, which is reflected by a modification in the microrelief of the skin, the appearance of wrinkles and uneven pigmentation (liver spots, lack of uniformity of the complexion).

Many photoprotective compositions have been proposed to date to overcome the effects induced by UV-A and/or UV-B radiation. They generally contain organic or mineral UV-screening agents, which function according to their own chemical nature and according to their own properties by absorption, reflection or scattering of the UV radiation. They generally contain mixtures of liposoluble organic screening agents and/or of water-soluble UV-screening agents combined with metal oxide pigments such as titanium dioxide or zinc oxide.

Fine mineral particles based on a metal oxide such as titanium dioxide ($TiO_2$) are usually used for children's skin or sensitive skin, to protect the skin against UV rays.

These fine metal oxide particles generally have a mean elementary particle size of less than or equal to 0.1 µm, preferably between 0.005 and 0.1 µm, preferably between 0.01 and 0.1 µm, and preferentially between 0.015 and 0.05 µm.

However, these particulate mineral screening agents have the drawback of degrading the cosmeticity of cosmetic compositions, by generating a white film on the skin during application.

Patent applications FR 2 882 371, WO 2006/083 326 and WO 98/37 964 describe various processes for manufacturing composite particles consisting of a material comprising nanoparticles of metal oxides, such as titanium dioxide.

Patent application WO 2006/061 835 describes compositions comprising spherical composites based on a metal oxide and on a hydrophobic polymer.

Known in the cosmetic field are patent application EP 1 388 550, which targets the use of composite particles comprising a core formed of a metal oxide coated with a silicone or fluoro compound and the use thereof as a photoprotective cosmetic composition, and patent application WO 98/22539, which describes a sunscreen containing a particle of silicon and/or another solid compound in which the silicon is in stoichiometric excess, the said particle having a mean diameter of less than 0.12 µm and being covered with a layer of oxide having a thickness ranging from 0.001 to 0.3 µm.

Patent applications WO 2012/105 723, WO 2012/105 059, WO 2012/104 160, WO 2012/104 161 and WO 2012/104 163 disclose composite particles for screening out UV radiation, with a mean size of greater than 0.1 µm and generally ranging up to 50 µm, comprising a matrix and at least one mineral UV-screening agent and/or at least one organic UV-screening agent. These screening materials have better cosmeticity and good photoprotective efficacy.

However, the particles of these composite UV-screening agents have a tendency rapidly to agglomerate and to sediment out in the antisun formulations commonly used, especially emulsions of the oil-in-water type (i.e. a cosmetically acceptable support consisting of an aqueous dispersing continuous phase and of an oily dispersed discontinuous phase) or of the water-in-oil type (i.e. a cosmetically acceptable support consisting of an oily dispersing continuous phase and an aqueous dispersed discontinuous phase). This has the consequence of destabilizing these compositions, making them unsuitable for consumption and of not producing on the surface of the area to be treated a homogeneous product uniformly distributed for good efficacy.

There is thus still a need to make antisun compositions based on composite particles for screening out UV radiation, with a mean size of greater than 0.1 µm, comprising a matrix and at least one mineral UV-screening agent with a good level of protection, without any agglomeration or sedimentation in the composition containing them.

The Applicant has discovered, surprisingly, that this object can be achieved by using hydrophobic silica aerogel particles in a composition based on this type of composite particle.

This discovery forms the basis of the present invention.

The present invention relates to a composition comprising, in a cosmetically acceptable medium:

a) at least composite particles with a mean size of greater than 0.1 μm, containing:
   i) a matrix comprising at least one organic material and/or at least one mineral material and
   ii) at least titanium dioxide, optionally treated with a surface agent; and
b) hydrophobic silica aerogel particles.

The invention also relates to a cosmetic process for caring for and/or making up human keratin materials, especially bodily or facial skin or the hair, comprising at least the application, to the surface of the keratin material, of a composition as defined previously.

The invention also relates to a non-therapeutic cosmetic process for limiting the darkening of the skin and/or improving the colour and/or uniformity of the complexion, comprising the application, to the surface of the keratin material, of a composition as defined previously.

The invention also relates to a non-therapeutic cosmetic process for preventing and/or treating the signs of ageing of a keratin material, comprising the application, to the surface of the keratin material, of a composition as defined previously.

The term "human keratin materials" means the skin (body, face, area around the eyes), hair, eyelashes, eyebrows, body hair, nails, lips or mucous membranes.

The term "cosmetically acceptable medium" means any medium that is compatible with the skin and/or its integuments, which has a pleasant colour, odour and feel, and which does not cause any unacceptable discomfort (stinging, tautness or redness) liable to discourage the consumer from using this composition.

The term "mineral UV-screening agent" means a molecule not comprising any carbon atoms in its structure and capable of screening out UV radiation between 280 and 400 nm.

The term "mineral UV-screening agent in free form" means that the mineral UV-screening agent present in the composition is not incorporated into the matrix and/or onto the surface of the matrix of the composite particles.

The terms "mean size" and "mean diameter" mean, in the case of spherical particles, the magnitude that can be determined by calculating the mean of the dimensions of approximately a hundred particles on an image with a scanning electron microscope.

The term "mean elementary size" means the size of non-aggregated particles.

Hydrophobic Silica Aerogel Particles

A composition according to the invention also comprises aerogel silica particles, which are intended to stabilize the composition according to the invention. Aerogels are ultralight porous materials, the first ones of which were made by Kristler in 1932.

They are generally synthesized via a sol-gel process in liquid medium and then dried by extraction of a supercritical fluid. The supercritical fluid most commonly used is supercritical $CO_2$. This type of drying makes it possible to avoid the contraction of the pores and of the material.

Other types of drying also make it possible to obtain porous materials from gel, namely (i) drying by cryodesiccation, which consists in solidifying the gel at low temperature and then in subliming off the solvent, and (ii) drying by evaporation. The materials thus obtained are then known, respectively, as cryogels and xerogels. The sol-gel process and the various drying operations are described in detail in Brinker C. J. and Scherer G. W., Sol-Gel Science, New York: Academic Press, 1990.

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

The hydrophobic silica aerogel particles used in the present invention have a specific surface area per unit of mass ($S_M$) ranging from 200 to 1500 $m^2/g$, preferably from 600 to 1200 $m^2/g$ and better still from 600 to 800 $m^2/g$, and a size, expressed as the volume-mean diameter (D[0.5]), of less than 1500 μm and preferably ranging from 1 to 30 μm, more preferentially from 5 to 25 μm, better still from 5 to 20 μm and even better still from 5 to 15 μm.

According to one advantageous embodiment, the hydrophobic silica aerogel particles have an oil-absorbing capacity, measured at the wet point, ranging from 5 to 18 ml/g, preferably from 6 to 15 ml/g and better still from 8 to 12 ml/g of particles.

The oil-absorbing capacity measured at the wet point, noted Wp, corresponds to the amount of oil that needs to be added to 100 g of particles in order to obtain a homogeneous paste.

It is measured according to the "wet point" method or method for determining the oil uptake of powder described in standard NF T 30-022. It corresponds to the amount of oil adsorbed onto the available surface of the powder and/or absorbed by the powder. The method is described below:

An amount m=2 g of powder is placed on a glass plate, and the oil (isononyl isononanoate) is then added dropwise. After addition of 4 to 5 drops of oil to the powder, mixing is performed using a spatula, and addition of oil is continued until conglomerates of oil and powder have formed. From this point, the oil is added one drop at a time and the mixture is then triturated with the spatula. The addition of oil is stopped when a firm and smooth paste is obtained. This paste must be able to be spread on the glass plate without cracking or forming lumps. The volume Vs (expressed in ml) of oil used is then noted.

The oil uptake corresponds to the ratio Vs/m.

The hydrophobic silica aerogel particles used according to the present invention are preferably aerogel particles of silylated silica (INCI name: silica silylate).

The preparation of hydrophobic silica aerogel particles surface-modified by silylation is further described in document U.S. Pat. No. 7,470,725.

Use will be made in particular of hydrophobic silica aerogel particles surface-modified with trimethylsilyl groups.

The hydrophobic silica aerogel particles that may be used in the present invention advantageously have a size, expressed as the mean diameter (D[0.5]), of less than 1500 μm, preferably ranging from 1 to 30 μm, preferably from 5 to 25 μm, better still from 5 to 20 μm and even better still from 5 to 15 μm.

The specific surface area per unit of mass may be determined via the BET (Brunauer-Emmett-Teller) nitrogen absorption method described in the *Journal of the American Chemical Society*, vol. 60, page 309, February 1938, which corresponds to International Standard ISO 5794/1 (appendix D). The BET specific surface area corresponds to the total specific surface area of the particles under consideration.

The sizes of the aerogel particles according to the invention can be measured by static light scattering using a commercial particle size analyzer such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., *Light Scattering by Small Particles*, Chapters 9 and 10, Wiley, New York, 1957.

According to one advantageous embodiment, the hydrophobic aerogel particles used in the present invention have a specific surface area per unit of mass ($S_M$) ranging from 600 to 800 m$^2$/g and a size, expressed as the volume-mean diameter (D[0.5]), ranging from 5 to 20 μm and better still from 5 to 15 μm.

The hydrophobic aerogel particles used in the present invention may advantageously have a tapped density ρ ranging from 0.04 g/cm$^3$ to 0.10 g/cm$^3$ and preferably from 0.05 g/cm$^3$ to 0.08 g/cm$^3$.

In the context of the present invention, this density can be assessed according to the following protocol, known as tapped density protocol:

40 g of powder are poured into a measuring cylinder and the cylinder is then placed on a Stay 2003 machine from Stampf Volumeter. The cylinder is subsequently subjected to a series of 2500 tapping actions (this operation is repeated until the difference in volume between two consecutive tests is less than 2%) and the final volume Vf of packed powder is then measured directly on the measuring cylinder.

The tapped density is determined by the ratio: mass (m)/Vf, in this instance 40/Vf (Vf being expressed in cm$^3$ and m in g).

According to one embodiment, the hydrophobic aerogel particles used in the present invention have a specific surface area per unit of volume SV ranging from 5 to 60 m$^2$/cm$^3$, preferably from 10 to 50 m$^2$/cm$^3$ and better still from 15 to 40 m$^2$/cm$^3$.

The specific surface area per unit of volume is given by the relationship: SV=SM*ρ,☐ where ρ is the tapped density, expressed in g/cm$^3$, and SM is the specific surface area per unit of mass, expressed in m$^2$/g, as defined above.

According to one embodiment, the hydrophobic silica aerogel particles have at least one of the following conditions and preferably all of the following conditions:
 a tapped density ρ ranging from 0.04 g/cm$^3$ to 0.10 g/cm$^3$ and preferably from 0.05 g/cm$^3$ to 0.08 g/cm$^3$;
 a specific surface area per unit of volume SV ranging from 5 to 60 m$^2$/cm$^3$, preferably from 10 to 50 m$^2$/cm$^3$ and better still from 15 to 40 m$^2$/cm$^3$;
 an oil-absorbing capacity, measured at the wet point, ranging from 5 to 18 ml/g, preferably from 6 to 15 ml/g and better still from 8 to 12 ml/g of particles.

As hydrophobic silica aerogels that may be used in the invention, an example that may be mentioned is the aerogel sold under the name VM-2270 (INCI name: Silica silylate) by the company Dow Corning, the particles of which have a mean size of about 1000 microns and a specific surface area per unit of mass ranging from 600 to 800 m$^2$/g.

Mention may also be made of the aerogels sold by the company Cabot under the references Aerogel TLD 201, Aerogel OGD 201 and Aerogel TLD 203, Enova Aerogel MT 1100 and Enova Aerogel MT 1200.

Use will more particularly be made of the aerogel sold under the name VM-2270 (INCI name: Silica silylate) by the company Dow Corning, the particles of which have a mean size ranging from 5 to 15 microns and a specific surface area per unit of mass ranging from 600 to 800 m$^2$/g.

The silica aerogel particles in accordance with the invention are preferably present in the cosmetic composition in an amount of active material ranging from 0.5% to 15% by weight and more preferentially from 1% to 10% by weight relative to the total weight of the composition.

Composite Particles for Screening Out UV Radiation

The composite particles in accordance with the invention comprise an organic and/or mineral matrix and at least titanium dioxide.

These composite particles may be chosen from spherical composite particles and non-spherical composite particles, or mixtures thereof.

The term "spherical" means that the particle has a sphericity index, i.e. the ratio of its largest diameter to its smallest diameter, of less than 1.2.

The term "non-spherical" means particles in three dimensions (length, width, thickness or height) for which the ratio of the greatest dimension to the smallest dimension is greater than 1.2. The dimensions of the particles of the invention are evaluated by scanning electron microscopy and image analysis. They comprise particles of parallelepipedal shape (rectangular or square surface), discoid shape (circular surface) or ellipsoid shape (oval surface), characterized by three dimensions: a length, a width and a height. When the shape is circular, the length and the width are identical and correspond to the diameter of a disc, whereas the height corresponds to the thickness of the disc. When the surface is oval, the length and the width correspond, respectively, to the large axis and the small axis of an ellipse and the height corresponds to the thickness of the elliptic disc formed by the platelet. When it is a parallelepiped, the length and the width may be of identical or different dimensions: when they are of the same dimension, the shape of the surface of the parallelepiped is a square; in the contrary case, the shape is rectangular. With regard to the height, it corresponds to the thickness of the parallelepiped.

The non-spherical composite particles of the invention are characterized by three dimensions:
 the smallest of which is greater than 0.1 μm, preferably greater than 0.3 μm and better still greater than 0.5 μm;
 the largest is less than 30 μm, preferably less than 20 μm and better still less than 10 μm.

The ratio of the largest to the smallest dimension is greater than 1.2.

The dimensions of the particles of the invention are evaluated by scanning electron microscopy and image analysis.

The non-spherical composite particles that may be used according to the invention will preferably be platelet-shaped.

The term "platelet-shaped" is understood to mean a parallelepipedal shape. They may be smooth, rough or porous.

The spherical and non-spherical screening composite particles used according to the present invention comprise a matrix and at least titanium dioxide.

a) Titanium Dioxide

Preferentially, the titanium dioxide particles have a mean elementary particle size of less than or equal to 0.5 μm, more preferentially between 0.005 and 0.5 μm, even more preferentially between 0.01 and 0.2 μm, better still between 0.01 and 0.1 μm and more particularly preferentially between 0.015 and 0.05 μm.

In particular, the titanium dioxide (TiO$_2$) can be in the rutile and/or anatase form and/or in an amorphous form.

Such coated or uncoated titanium dioxide pigments are described in particular in patent application EP-A-0 518

773. Commercial pigments that may be mentioned include the products sold by the companies Sachtleben Pigments, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

The coated pigments are more particularly titanium oxides that have been coated:
  with silica, such as the product Sunveil from the company Ikeda,
  with silica and iron oxide, such as the product Sunveil F from the company Ikeda,
  with silica and alumina, such as the products Microtitanium Dioxide MT 500 SA and Microtitanium Dioxide MT 100 SA from the company Tayca and Tioveil from the company Tioxide,
  with alumina, such as the products Tipaque TTO-55 (B) and Tipaque TTO-55 (A) from the company Ishihara and UVT 14/4 from the company Sachtleben Pigments,
  with alumina and aluminium stearate, such as the products Microtitanium Dioxide MT 100 T, MT 100 TX, MT 100 Z and MT-01 from the company Tayca, the products Solaveil CT-10 W and Solaveil CT 100 from the company Uniqema and the product Eusolex T-AVO from the company Merck,
  with silica, alumina and alginic acid, such as the product MT-100 AQ from the company Tayca,
  with alumina and aluminium laurate, such as the product Microtitanium Dioxide MT 100 S from the company Tayca,
  with iron oxide and iron stearate, such as the product Microtitanium Dioxide MT 100 F from the company Tayca,
  with zinc oxide and zinc stearate, such as the product BR 351 from the company Tayca,
  with silica and alumina and treated with a silicone, such as the products Microtitanium Dioxide MT 600 SAS, Microtitanium Dioxide MT 500 SAS or Microtitanium Dioxide MT 100 SAS from the company Tayca,
  with silica, alumina and aluminium stearate and treated with a silicone, such as the product STT-30-DS from the company Titan Kogyo,
  with silica and treated with a silicone, such as the product UV-Titan X 195 from the company Sachtleben Pigments,
  with alumina and treated with a silicone, such as the products Tipaque TTO-55 (S) from the company Ishihara or UV Titan M 262 from the company Sachtleben Pigments,
  with triethanolamine, such as the product STT-65-S from the company Titan Kogyo,
  with stearic acid, such as the product Tipaque TTO-55 (C) from the company Ishihara,
  with sodium hexametaphosphate, such as the product Microtitanium Dioxide MT 150 W from the company Tayca,
  $TiO_2$ treated with octyltrimethylsilane, sold under the trade name T 805 by the company Degussa Silices,
  $TiO_2$ treated with a polydimethylsiloxane, sold under the trade name 70250 Cardre UF TiO2SI3 by the company Cardre,
  anatase/rutile $TiO_2$ treated with a polydimethylhydrosiloxane, sold under the trade name Microtitanium Dioxide USP Grade Hydrophobic by the company Color Techniques.

The uncoated titanium oxide pigments are sold, for example, by the company Tayca under the trade names Microtitanium Dioxide MT 500 B or Microtitanium Dioxide MT 600 B, by the company Degussa under the name P 25, by the company Wackher under the name Transparent titanium oxide PW, by the company Miyoshi Kasei under the name UFTR, by the company Tomen under the name ITS and by the company Tioxide under the name Tioveil AQ.

The mass content of titanium dioxide in the composite particles of the invention is preferably from 1% to 90% by weight, preferably from 2% to 80% by weight and better still from 3% to 70% by weight, relative to the total weight of a composite particle.

c) Structure of the Screening Composite Material

According to a first variant, the composite particles contain a matrix comprising an organic and/or mineral material, in which matrix are included titanium dioxide particles. According to this embodiment, the matrix has inclusions and titanium dioxide particles are placed in the inclusions of the matrix.

According to a second alternative form, the composite particles comprise a matrix made of an organic and/or mineral material, which matrix is covered with at least one layer of titanium dioxide which may be connected to the matrix by means of a binder.

According to a third variant, the composite particles contain at least titanium dioxide covered with at least one layer of an organic and/or mineral material.

The matrix may also be formed from one or more organic or mineral materials. It may then be a continuous phase of materials such as an alloy, i.e. a continuous phase in which the materials can no longer be dissociated, or a discontinuous phase of materials, for example consisting of an organic or mineral material covered with a layer of another different organic or mineral material.

According to one variant, in particular when the composite particles comprise a matrix covered with a layer of titanium dioxide, the composite particles may furthermore be covered with an additional coating, in particular chosen from biodegradable or biocompatible materials, lipid materials, for instance surfactants or emulsifiers, polymers, and oxides.

The mineral materials that may be used in the matrix of the composite particles according to the present invention may be chosen from the group formed by mica, synthetic mica, talc, sericite, boron nitride, glass flakes, calcium carbonate, barium sulfate, titanium oxide, hydroxyapatite, silica, a silicate, zinc oxide, magnesium sulfate, magnesium carbonate, magnesium trisilicate, aluminium oxide, calcium silicate, calcium phosphate, magnesium oxide, bismuth oxychloride, kaolin, hydrotalcite, a mineral or synthetic clay, and iron oxide, and mixtures thereof.

The organic materials that may be used to form the matrix are chosen from the group formed by poly(meth)acrylates, polyamides, silicones, polyurethanes, polyethylenes, polypropylenes, polystyrenes, styrene copolymers, polyhydroxyalkanoates, polycaprolactams, poly(butylene)succinates, polysaccharides, polypeptides, polyvinyl alcohols, polyvinyl resins, fluoro polymers, waxes, polyesters, polyethers, multivalent metal salts of amidosulfonic acid, and acylated amino acids, and mixtures thereof.

A fluoro polymer that may be mentioned is polytetrafluoroethylene (PTFE), such as the commercial product Ceridust 9205F® sold by the company Clariant.

An example of a multivalent metal salt of amidosulfonic acid that may be mentioned is calcium N-lauroyltaurine.

An acylated amino acid that may be mentioned is lauroyllysine.

Polyamides that may be mentioned include polyamide-6 or polyamide-12 (Nylon®) or the commercial products SP-500® sold by the company Toray and Orgasol® by the company Arkema. The process for obtaining these particles is, for example, the one described in document FR 2 619 385 or in document EP 303 530. The particles have a density ranging from 1 $g/cm^3$ to 1.84 $g/cm^3$ and in particular a density ranging from 1.0 $g/cm^3$ to 1.4 $g/cm^3$. They are generally spherical and filled; they especially have mean sizes ranging from 5 µm to 50 µm and more particularly ranging from 10 µm to 30 µm.

Polyhydroxyalkanoates that may be mentioned are polylactic acids.

Poly(meth)acrylates that may be mentioned are polymethyl methacrylates, such as the commercial product sold under the trade names MR-7GC®, MP-2200®, MP-2701® and MP-1451® by the company Soken, Japan.

Styrene copolymers that may be mentioned are hollow spherical particles of a copolymer of styrene and of (meth)acrylic acid or a $(C_1-C_{20})$alkyl ester thereof, under the INCI name: Styrene/Acrylates Copolymer, for instance the product sold under the trade name Sunspheres Powder by the company Röhm & Haas, and the particles of styrene/methyl methacrylate crosslinked copolymer sold under the trade names SX859(A)® and SX866(B)® by the company JSR Corp., Japan.

Preferably, the matrix of the composite particle contains a material or a mixture of materials chosen from:
  silica,
  talc,
  mica,
  alumina,
  an alumina/triethoxycaprylylsilane mixture,
  polymethyl methacrylate (PMMA),
  copolymers of styrene and of (meth)acrylic acid or a $(C_1-C_{20})$alkyl ester thereof,
  polyamides such as polyamide-6 or polyamide-12,
  and mixtures thereof.

As spherical composite particles consisting of a matrix comprising an organic and/or mineral material, in which matrix are included titanium dioxide particles, mention may be made of the products Sunsil TIN 50 and Sunsil TIN 40 sold by the company Sunjin Chemical. These spherical composite particles with a mean size of between 2 and 7 µm are formed of $TiO_2$ encapsulated in a silica matrix.

Mention may also be made of the following particles:
  spherical composite particles with a mean size between 4 and 8 µm, containing $TiO_2$ and $SiO_2$ and having the trade name Eospoly TR® sold by the company Créations Couleurs,
  composite particles containing $TiO_2$ and a styrene/alkyl acrylate copolymer matrix sold under the name Eospoly UV TR22 HB 50® by the company Creations Couleurs,
  composite particles containing $TiO_2$ and ZnO and a PMMA matrix and having the trade name Sun PMMA-T50® sold by the company Sunjin Chemical.

As spherical composite particles consisting of a matrix comprising an organic and/or mineral material and covered with at least one layer of titanium dioxide connected to the matrix by means of a binder, mention is made of spherical composite particles containing $TiO_2$ and $SiO_2$, having the trade name STM ACS-0050510 supplied by the company JGC Catalysts and Chemical.

The mean thickness of the layer of titanium dioxide is generally approximately ten nanometers. The mean thickness of the layer of mineral UV-screening agent is advantageously between 0.001 and 0.2 µm and preferably between 0.001 and 0.2 µm.

As lamellar composite particles according to the invention, consisting of a matrix comprising an organic and/or mineral material and covered with at least one layer of titanium dioxide connected to the matrix by means of a binder, mention may be made of the following particles:
  composite particles containing $TiO_2$ and an alumina matrix, having the trade name Matlake OPA® sold by the company Sensient LCW,
  composite particles containing $TiO_2$ and an alumina/triethoxycaprylylsilane matrix, having the trade name Matlake OPA AS®, sold by the company Sensient LCW,
  composite particles comprising ultrafine $TiO_2$ particles deposited on the surface of talc platelets, having the trade name TTC 30®, sold by the company Miyoshi Kasei,
  composite particles comprising ultrafine $TiO_2$ particles deposited on the surface of talc platelets, having the trade name Silseem Mistypearl Yellow®, sold by the company Nihon Koken Kogyo (NKK).

According to a particular form of the invention, the composite particles comprise at least one core particle A with a mean size of greater than 0.1 µm and less than 1 µm, preferably less than 0.6 µm and even more preferentially less than 0.4 µm; the surface of the said core being at least partially covered with at least one layer of titanium dioxide.

The core particle may have any shape, for example it may be in the form of a plate with a shape factor of at least 5, preferably greater than 10, more preferentially greater than 20 and more particularly greater than 50. The shape factor may be determined by the ratio of the mean length to the mean thickness.

If the core particle of the invention is platelet-shaped, its length is greater than 0.1 and less than 1 µm, preferably less than 0.6 µm and even more preferentially less than 0.4 µm.

Preferentially, the core particle A has a spherical shape.

The core particle A may comprise at least one organic and/or mineral material such as those described previously.

The organic material and/or the mineral material may be hollow or porous. The porosity of the said materials may be characterized by a specific surface area preferably of from 0.05 $m^2/g$ to 1500 $m^2/g$, more preferentially from 0.1 $m^2/g$ to 1000 $m^2/g$ and even more preferentially from 0.2 $m^2/g$ to 500 $m^2/g$ according to the BET method.

The core particle A may optionally be precoated. The coating material may especially be organic, chosen from an amino acid, an N-acylamino acid, an amide, a silicone or a modified silicone, in particular lauroyllysine and an acrylic-modified silicone.

The core particle A is at least partially covered with at least one layer comprising at least titanium dioxide as defined previously. Preferentially, at least 10% of the surface of the core particle A may be covered with one or more layers. More preferentially, at least 50% and more particularly 80% or even 100% of the surface of the core particle A may be covered with one or more layers.

The thickness of a coating layer may vary as a function of several factors, especially as a function of the size of the core particle A. Typically, the thickness of a coating layer may range from 0.001 to 0.005 µm, preferably from 0.005 to 0.004 µm and more preferentially from 0.01 to 0.03 µm.

If there are at least two coating layers on the core particle A, the thickness of the various layers and the composition thereof may be identical or different.

The coating layer(s) may also contain an additive other than titanium dioxide, especially a colouring pigment and/or an organic UV-screening agent. The additive(s) may be present in an amount ranging from 1% to 50% by weight relative to the total weight of the mixture of mineral UV-screening agents and of the additive(s).

Colouring Pigments

The term "colouring pigment" should be understood as meaning any white or coloured, mineral or organic particle, of any form, which is insoluble and/or intended to colour the composition containing it.

The colouring pigments generally have a mean particle size of at least 0.1 µm.

Among the mineral pigments that may be mentioned are titanium dioxide, optionally surface-treated, zirconium oxide, cerium oxide, zinc oxide, iron oxides (black, yellow or red), chromium oxide, manganese violet, ultramarine blue, chromium hydrate, ferric blue and barium sulfate, and metal powders such as aluminium, copper, silver or gold.

According to a particular mode, the mean size of the colouring pigment may range from at least 0.001 µm to less than 1 µm, preferably from at least 0.001 µm to less than 0.5 µm and more preferentially from 0.001 µm to less than 0.3 µm.

Among the organic pigments, mention may be made of carbon black pigments, pigments of the D&C type and lakes, such as lakes based on cochineal carmine, barium, strontium, calcium or aluminium. For example, Red 202 (calcium bis[2-(3-carboxy-2-hydroxynaphthylazo)-5-methylbenzenesulfonate) may be used as pigment of the D&C type.

Preferably, the coloured pigments are chosen from titanium dioxide, zirconium oxide, cerium oxide, zinc oxide, iron oxide, manganese violet, ultramarine blue, chromium hydrate, ferric blue, metal powders such as aluminium, copper, silver or gold, barium sulfate, carbon black, pigments of the D&C type, lakes and nacreous pigments, and mixtures thereof.

The term "nacreous pigment" means any iridescent particle of any form, such as the particles produced by certain shells or synthetic particles.

The nacreous agents may be chosen from white pigments such as mica coated with titanium dioxide or with bismuth oxychloride, coloured nacreous pigments such as iron oxides, micas coated with titanium dioxide coated with ferric blue or with chromium oxide, iron oxide, mica treated with titanium dioxide coated with ferric blue or with chromium oxide or an organic pigment such as those described previously, and nacreous pigments based on bismuth oxychloride.

Organic UV-Screening Agents

The additional organic UV-screening agents are chosen especially from cinnamic compounds; anthranilate compounds; salicylic compounds; dibenzoylmethane compounds; benzylidenecamphor compounds; benzophenone compounds; β,β-diphenylacrylate compounds; triazine compounds; benzotriazole compounds; benzalmalonate compounds, especially those cited in U.S. Pat. No. 5,624,663; benzimidazole derivatives; imidazoline compounds; bis-benzazolyl compounds, as described in patents EP 669 323 and U.S. Pat. No. 2,463,264; p-aminobenzoic acid (PABA) compounds; methylenebis(hydroxyphenylbenzotriazole) compounds, as described in patent applications U.S. Pat. No. 5,237,071, U.S. Pat. No. 5,166,355, GB 2 303 549, DE 197 26 184 and EP 893 119; benzoxazole compounds, as described in patent applications EP 0 832 642, EP 1 027 883, EP 1 300 137 and DE 101 62 844; screening polymers and screening silicones, such as those described in particular in patent application WO 93/04665; α-alkylstyrene-based dimers, such as those described in patent application DE 198 55 649; 4,4-diarylbutadiene compounds, as described in patent applications EP 0 967 200, DE 197 46 654, DE 197 55 649, EP-A-1 008 586, EP 1 133 980 and EP 133 981, and mixtures thereof.

As examples of organic photoprotective agents, mention may be made of those denoted hereinbelow under their INCI name:

Cinnamic Compounds:
Ethylhexyl methoxycinnamate sold especially under the trade name Parsol MCX® by DSM Nutritional Products,
Isopropyl methoxycinnamate,
Isoamyl p-methoxycinnamate sold under the trade name Neo Heliopan E 1000® by Symrise,
DEA Methoxycinnamate,
Diisopropyl methylcinnamate,
Glyceryl Ethylhexanoate Dimethoxycinnamate.

Para-Aminobenzoic Compounds:
PABA,
Ethyl PABA,
Ethyl dihydroxypropyl PABA,
Ethylhexyl dimethyl PABA, sold in particular under the name Escalol 507® by ISP,
Glyceryl PABA,
PEG-25 PABA, sold under the name Uvinul P 25® by BASF.

Salicylic Compounds:
Homosalate, sold under the name Eusolex HMS® by Rona/EM Industries,
Ethylhexyl salicylate, sold under the name Neo Heliopan OS® by Symrise,
Dipropylene glycol salicylate, sold under the name Dipsal® by Scher,
TEA Salicylate, sold under the name Neo Heliopan TS® by Symrise.

Dibenzoylmethane Compounds:
Butyl Methoxydibenzoylmethane or Avobenzone, sold in particular under the trade name Parsol 1789® by DSM Nutritional Products.

β,β-Diphenylacrylate Compounds:
Octocrylene, sold in particular under the trade name Uvinul N 539® by BASF,
Etocrylene, sold in particular under the trade name Uvinul N 35® by BASF.

Benzophenone Compounds:
Benzophenone-1, sold under the trade name Uvinul 400® by BASF,
Benzophenone-2, sold under the trade name Uvinul D 50® by BASF,
Benzophenone-3 or Oxybenzone, sold under the trade name Uvinul M 40® by BASF,
Benzophenone-4, sold under the trade name Uvinul MS 40® by BASF,
Benzophenone-5,
Benzophenone-6, sold under the trade name Helisorb 11® by Norquay, Benzophenone-8, sold under the trade name Spectra-Sorb UV-24® by American Cyanamid, Benzophenone-9, sold under the trade name Uvinul DS 49® by BASF, Benzophenone-12, n-Hexyl 2-(4-diethylamino-2-hydroxybenzoyl)benzoate, sold under the trade name Uvinul A Plus® or, as a mixture with octyl methoxycinnamate, under the trade name Uvinul A Plus B® by BASF, 1,1'-(1,4-Piperazinediyl)bis[1-[2-[4-(diethylamino)-2-hydroxybenzoyl]phenyl]methanone] (CAS 919803-06-8), such as described in patent application WO 2007/071 584; this compound advantageously being used in micronized form (mean size of 0.02 to 2 µm), which may be obtained, for example, according to the micronization process described in patent applications GB-A-2 303 549 and EP-A-893 119, and especially in the form of an aqueous dispersion.

Benzylidenecamphor Compounds:

3-Benzylidenecamphor, manufactured under the name Mexoryl SD® by Chimex,

4-Methylbenzylidenecamphor, sold under the name Eusolex 6300® by Merck,

Benzylidenecamphorsulfonic acid, manufactured under the name Mexoryl SL® by Chimex, Camphor benzalkonium methosulfate, manufactured under the name Mexoryl SO® by Chimex, Terephthalylidenedicamphorsulfonic acid, manufactured under the name Mexoryl SX® by Chimex, Polyacrylamidomethylbenzylidenecamphor, manufactured under the name Mexoryl SW® by Chimex.

Phenylbenzimidazole Compounds:

Phenylbenzimidazolesulfonic acid, sold in particular under the trade name Eusolex 232® by Merck.

Bis-Benzazolyl Compounds:

Disodium Phenyl Dibenzimidazole Tetrasulfonate, sold under the trade name Neo Heliopan AP® by Haarmann and Reimer.

Phenylbenzotriazole Compounds:

Drometrizole trisiloxane, sold under the name Silatrizole® by Rhodia Chimie.

Methylenebis(Hydroxyphenylbenzotriazole) Compounds:

Methylene Bis-Benzotriazolyl Tetramethylbutylphenol, especially in solid form, such as the product sold under the trade name Mixxim BB/100® by Fairmount Chemical, or in the form of an aqueous dispersion of micronized particles with a mean particle size ranging from 0.01 to 5 µm, more preferentially from 0.01 to 2 µm and more particularly from 0.020 to 2 µm, with at least one alkylpolyglycoside surfactant having the structure $C_nH_{2n+1}O(C_6H_{10}O_5)_xH$, in which n is an integer from 8 to 16 and x is the mean degree of polymerization of the $(C_6H_{10}O_5)$ unit and ranges from 1.4 to 1.6, as described in patent GB-A-2 303 549, sold in particular under the trade name Tinosorb M® by the company BASF, or in the form of an aqueous dispersion of micronized particles with a mean particle size ranging from 0.02 to 2 µm, more preferentially from 0.01 to 1.5 µm and more particularly from 0.02 to 1 µm, in the presence of at least one polyglyceryl mono($C_8$-$C_{20}$)alkyl ester with a degree of glycerol polymerization of at least 5, such as the aqueous dispersions described in patent application WO 2009/063 392.

Triazine Compounds:

Bis-Ethylhexyloxyphenol Methoxyphenyl Triazine, sold under the trade name Tinosorb S® by BASF, Ethylhexyl Triazone, sold in particular under the trade name Uvinul T150® by BASF, Diethylhexyl Butamido Triazone, sold under the trade name Uvasorb HEB® by Sigma 3V, 2,4,6-tris(dineopentyl 4'-aminobenzalmalonate)-s-triazine, 2,4,6-tris(diisobutyl 4'-aminobenzalmalonate)-s-triazine, 2,4-bis(n-butyl 4'-aminobenzoate)-6-(aminopropyltrisiloxane)-s-triazine, 2,4-bis(dineopentyl 4'-aminobenzalmalonate)-6-(n-butyl 4'-aminobenzoate)-s-triazine, symmetrical triazine screening agents substituted with naphthalenyl groups or polyphenyl groups described in U.S. Pat. No. 6,225,467, patent application WO 2004/085 412 (see compounds 6 and 9) or the document "Symmetrical Triazine Derivatives", IP.COM IPCOM000031257 Journal, INC, West Henrietta, N.Y., US (20 Sep. 2004), in particular 2,4,6-tris(diphenyl)triazine and 2,4,6-tris(terphenyl)triazine, which is also mentioned in patent applications WO 06/035 000, WO 06/034 982, WO 06/034 991, WO 06/035 007, WO 2006/034 992 and WO 2006/034 985, these compounds advantageously being used in micronized form (mean particle size of 0.02 to 3 µm), which may be obtained, for example, according to the micronization process described in patent applications GB-A-2 303 549 and EP-A-893 119, and in particular in aqueous dispersion;

silicone triazines substituted with two aminobenzoate groups, as described in patent EP 0 841 341, in particular 2,4-bis(n-butyl 4'-aminobenzalmalonate)-6-[(3-{1,3,3,3-tetramethyl-1-[(trimethylsilyl)oxy]disiloxanyl}propyl) amino]-s-triazine.

Anthranilic Compounds:

Menthyl anthranilate, sold under the trade name Neo Heliopan MA® by Symrise.

Imidazoline Compounds:

Ethylhexyl dimethoxybenzylidene dioxoimidazoline propionate.

Benzalmalonate Compounds:

Polyorganosiloxane comprising benzalmalonate functional groups, such as Polysilicone-15, sold under the trade name Parsol SLX® by Hoffmann LaRoche.

4,4-Diarylbutadiene Compounds:

1,1-Dicarboxy(2,2'-dimethylpropyl)-4,4-diphenylbutadiene.

Benzoxazole Compounds:

2,4-bis[5-(1,1-dimethylpropyl)benzoxazol-2-yl(4-phenyl) imino]-6-(2-ethylhexyl)imino-1,3,5-triazine, sold under the name Uvasorb K2A® by Sigma 3V.

The preferred organic screening agents are chosen from:
Ethylhexyl methoxycinnamate,
Butylmethoxydibenzoylmethane,
Ethylhexyl salicylate,
Homosalate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyl dibenzimidazole tetrasulfonate,
Methylenebis(benzotriazolyl)tetramethylbutylphenol,
Bis(ethylhexyloxyphenol)methoxyphenyltriazine,
Ethylhexyl Triazone,
Diethylhexyl Butamido Triazone,
2,4,6-Tris(dineopentyl 4'-aminobenzalmalonate)-s-triazine,
2,4,6-Tris(diisobutyl 4'-aminobenzalmalonate)-s-triazine, 2,4-Bis(n-butyl 4'-aminobenzoate)-6-(aminopropyltrisiloxane)-s-triazine,
2,4-Bis(dineopentyl 4'-aminobenzalmalonate)-6-(n-butyl 4'-aminobenzoate)-s-triazine,
2,4-Bis(n-butyl 4'-aminobenzalmalonate)-6-[(3-{1,3,3,3-tetramethyl-1-[(trimethylsilyl)oxy]disiloxanyl}propyl)amino]-s-triazine,
2,4,6-Tris(diphenyl)triazine,
2,4,6-Tris(terphenyl)triazine,
Drometrizole Trisiloxane,
Polysilicone-15,
1,1-Dicarboxy(2,2'-dimethylpropyl)-4,4-diphenylbutadiene,
2,4-Bis[4-[5-(1,1-dimethylpropyl)benzoxazol-2-yl]phenylimino]-6-[(2-ethylhexyl)imino]-1,3,5-triazine,
and mixtures thereof.

The particularly preferred organic screening agents are chosen from:
Butyl Methoxydibenzoylmethane,
Ethylhexyl salicylate,
Homosalate,
Octocrylene,
n-Hexyl 2-(4-diethylamino-2-hydroxybenzoyl)benzoate,
Terephthalylidenedicamphorsulfonic acid,
Bis(ethylhexyloxyphenol)methoxyphenyltriazine,
Ethylhexyl Triazone,
Diethylhexyl Butamido Triazone,
2,4-Bis(n-butyl 4'-aminobenzalmalonate)-6-[(3-{1,3,3,3-tetramethyl-1-[(trimethylsilyl)oxy]disiloxanyl}propyl)amino]-s-triazine,
Drometrizole Trisiloxane,
and mixtures thereof.

The composite particles of the invention comprising a core particle A may be prepared by subjecting the said core particle A, titanium dioxide and optionally the additive(s) to a mechanochemical melting process.

A mechanochemical melting process means a process in which a mechanical force such as an impact, a friction force or a shear force is exerted on a plurality of compounds, to produce partial melting of the various compounds.

The mechanochemical melting process may be performed, for example, with a machine comprising a rotary chamber and an internal fixed part with a scraper, such as the mechanofusion device of the Japanese brand Hosokawa Micron Corporation®.

It is preferable to use a hybridizer process as mechanochemical melting process.

The hybridizer process was developed in the 1980s. The hybridizer process is a type of mechanochemical melting process in which a strong mechanical force is applied to a plurality of particles in order to produce a mechanochemical reaction and to form a composite particle.

According to the hybridizer process, the mechanical force is exerted by a high-speed rotor which may have a diameter from 10 cm to 1 m and which can rotate at a speed from 1000 to 100 000 revolutions/minute. Thus, the hybridizer process may be defined as a mechanochemical melting process using a high-speed rotor. The hybridizer process is performed in the presence of air or under dry conditions. Specifically, on account of the high speed of the rotor, a high-speed air stream may be produced close to the rotor. Some liquid materials can be subjected to the hybridizer process in the presence of solid materials. The term "hybridizer process" has been used as the technical term in the present description. The hybridizer process may be performed using a hybridization system of the Japanese brand Nara Machinery®, in which at least two types of particles, typically core particles and fine particles, are introduced into a hybridizer equipped with a high-speed rotor having a plurality of blades in a dry chamber. The particles are dispersed in the chamber and mechanical and thermal energy (i.e. compression, friction, shear force) are exerted on the particles for a short period of time such as from 1 to 10 minutes and preferably from 1 to 5 minutes. This results in particles of one type (i.e. fine particles) integrated into or attached to particles of another type (core particles) so as to form composite particles. It is preferable for the particles to have been subjected to one or more electrostatic treatments such as buffeting to form an "ordered mixture" in which one type of particle is spread out to cover the other type of particle. The hybridizer process may also be performed by using a theta composter of the Japanese brand Tokuju Corporation®.

The hybridizer process may be performed with a Composi Hybrid® or Mechano Hybrid® device sold by the company Nippon Coke.

According to the present invention, the core particles A, the mineral screening agent(s) and optionally the additive(s) may be introduced into a hybridizer to form a composite pigment. The hybridizer process may be performed using a rotor rotating at 8000 rpm (100 m/sec) for approximately 3 minutes.

The core particle A, the titanium dioxide and optionally the additive(s) may be used in proportions such that the core particle/UV-screening agents and additives weight ratio ranges from 50/50 to 90/10, preferably from 50/50 to 80/20 and more preferentially from 50/50 to 70/30.

Furthermore, the hybridizer process can create an ordered assembly (uniform coating) of the mineral UV-screening agent(s) and optionally of the additive(s) on the core particle A and produce strong bonds on the surface of the core particle and the coating layer comprising the titanium dioxide and optionally the additive(s).

It should be noted that the hybridizer process is very different from other processes using, for example, a ball mill and a jet mill. Specifically, ball mills bring about spraying or agglomeration of the core particles, and jet mills bring about spraying of the core particles, making it difficult to uniformly coat the core particles with fine particles.

If necessary, an additional process may be performed to cover the composite material of the invention with an additional coating with mineral UV-screening agents and optionally additives such as pigments.

According to a particular form of the invention, the composite particles may comprise:

a) at least one core particle A with a mean size of greater than 0.1 µm and less than 1 µm, preferably less than 0.6 µm and even more preferentially less than 0.4 µm; the surface of the said core being at least partially covered with at least one layer of titanium dioxide, and b) at least one core particle B with a mean size of at least 2 µm, preferably of at least 3 µm, more preferentially of at least 4 µm and even more preferentially of at least 5 µm; the surface of the said core being at least partially covered with at least one layer of titanium dioxide.

The mean size of the core particles B is preferably less than or equal to 50 µm, more preferentially less than or equal to 30 µm, even more preferentially less than or equal to 20 µm and more particularly less than or equal to 10 µm.

The core particle B may have any shape, for example it may be in the form of a plate with a shape factor of at least 5, preferably greater than 10, more preferentially greater than 20 and more particularly greater than 50. The shape factor may be determined by the ratio of the mean length to the mean thickness.

If the core particle B of the invention is platelet-shaped, its length is greater than 0.1 µm and less than 1 µm, preferably less than 0.6 µm and even more preferentially less than 0.4 µm.

Preferentially, the core particle B has a spherical shape.

The core particle B may comprise at least one organic and/or mineral material such as those described previously.

The organic material and/or the mineral material may be hollow or porous. The porosity of the said materials may be characterized by a specific surface area preferably of from 0.05 m$^2$/g to 1500 m$^2$/g, more preferentially from 0.1 m$^2$/g to 1000 m$^2$/g and even more preferentially from 0.2 m$^2$/g to 500 m$^2$/g according to the BET method.

The core particle B may optionally be precoated. The coating material may especially be organic, chosen from an amino acid, an N-acylamino acid, an amide, a silicone or a modified silicone, in particular chosen from lauroyllysine and an acrylic-modified silicone.

The core particle B is at least partially covered with at least one layer comprising at least titanium dioxide as defined previously. Preferentially, at least 10% of the surface of the core particle A may be covered with one or more layers. More preferentially, at least 50% and more particularly 80% or even 100% of the surface of the core particle A may be covered with one or more layers.

The thickness of a coating layer may vary as a function of several factors, especially as a function of the size of the core particle B. Typically, the thickness of a coating layer may range from 0.001 to 0.03 µm and preferably from 0.005 to 0.03 µm.

If there are at least two coating layers on the core particle B, the thickness of the various layers and their composition may be identical or different.

The coating layer(s) may also contain an additive other than titanium dioxide, especially a colouring pigment. The additive(s) may be present in an amount ranging from 1% to 50% by weight relative to the total weight of the mixture of UV-screening agents and of the additive(s).

In the composition of these composite materials, the weight ratio of the core particles A to the core particles B is preferably from 10/90 to 90/10, more preferentially from 20/80 to 80/20 and more particularly from 30/70 to 70/30.

The particles A/particles B/TiO$_2$ weight ratio is preferably from 9/81/10 to 27/3/70, more preferentially from 8/72/20 to 45/5/50 and more particularly from 7/63/30 to 63/7/30.

According to a particular mode, the particles A/particles B/TiO$_2$ weight ratio is more preferentially from 20/50/30 to 50/20/30 or from 35/15/50 to 15/35/50.

These composite particles are preferably prepared according to a mechanochemical melting process using a hybridizer process as described previously. According to the present invention, the core particles A, the core particles B, the titanium dioxide and optionally the additive(s) may be introduced into a hybridizer to form a composite pigment.

According to a particularly preferred form of the invention, the composite particles comprise:

a) at least one hollow spherical core particle A with a mean size of greater than 0.1 µm and less than 1 µm, preferably less than 0.6 µm and even more preferentially less than 0.4 µm, comprising at least one copolymer of styrene and of (meth)acrylic acid or a (C$_1$-C$_{20}$)alkyl ester thereof; the surface of the said core A being at least partially covered with at least one layer of titanium dioxide as defined previously, preferably of the metal oxide type and more particularly titanium dioxide;

b) at least one spherical core particle B with a mean size of at least 2 µm, preferably of at least 3 µm, more preferentially of at least 4 µm and even more preferentially of at least 5 µm, comprising at least one poly(meth)acrylate and more preferentially a polymethyl methacrylate polymer; the surface of the said core B being at least partially covered with at least one layer of titanium dioxide.

Titanium dioxide is preferably present, in the compositions of the invention, in concentrations ranging from 1% to 70% by weight, preferably from 1.5% to 50% by weight and preferably from 2% to 40% by weight, relative to the total weight of the cosmetic composition.

Dextrin Ester

According to a particularly preferred form of the invention, the composition according to the invention also comprises at least one dextrin ester. In particular, the composition preferably comprises at least one preferably C$_{12}$-C$_{24}$ and in particular C$_{14}$-C$_{18}$ fatty acid ester of dextrin.

Addition of the dextrin ester makes it possible, firstly, in combination with the hydrophobic silica aerogel particles, to reduce or even eliminate the phenomena of agglomeration and sedimentation of the screening composite particles in the composition containing them, and, secondly, to give the surface of the keratin material a smooth effect after application of the composition.

Preferably, the dextrin ester is an ester of dextrin and of a C$_{12}$-C$_{18}$ and in particular C$_{14}$-C$_{18}$ fatty acid.

Preferably, the dextrin ester is chosen from dextrin myristate and/or dextrin palmitate, and mixtures thereof.

According to a particular embodiment, the dextrin ester is dextrin myristate, especially such as the product sold under the name Rheopearl MKL-2 by the company Chiba Flour.

According to a preferred embodiment, the dextrin ester is dextrin palmitate. This product may be chosen, for example, from those sold under the names Rheopearl TL® and Rheopearl KL® by the company Chiba Flour.

The composition according to the invention may particularly preferably comprise from 0.1% to 10% by weight and preferably from 0.5% to 5% by total weight of dextrin palmitate relative to the total weight of the composition, especially such as the products sold under the names Rheopearl TL® and Rheopearl KL® by the company Chiba Flour.

Oily Phase

The compositions in accordance with the invention preferably comprise at least one oily phase.

For the purposes of the invention, the term "oily phase" means a phase comprising at least one oil and all of the liposoluble and lipophilic ingredients and the fatty substances used for the formulation of the compositions of the invention.

The term "oil" means any fatty substance that is in liquid form at room temperature (20-25° C.) and at atmospheric pressure (760 mmHg).

An oil that is suitable for use in the invention may be volatile or non-volatile.

An oil that is suitable for use in the invention may be chosen from hydrocarbon-based oils, silicone oils and fluoro oils, and mixtures thereof.

A hydrocarbon-based oil that is suitable for use in the invention may be an animal hydrocarbon-based oil, a plant hydrocarbon-based oil, a mineral hydrocarbon-based oil or a synthetic hydrocarbon-based oil.

An oil that is suitable for use in the invention may be advantageously chosen from mineral hydrocarbon-based oils, plant hydrocarbon-based oils, synthetic hydrocarbon-based oils and silicone oils, and mixtures thereof.

For the purposes of the present invention, the term "silicone oil" is intended to mean an oil comprising at least one silicon atom, and in particular at least one Si—O group.

The term "hydrocarbon-based oil" means an oil comprising mainly hydrogen and carbon atoms.

The term "fluoro oil" means an oil comprising at least one fluorine atom.

A hydrocarbon-based oil that is suitable for use in the invention may also optionally comprise oxygen, nitrogen, sulfur and/or phosphorus atoms, for example in the form of hydroxyl, amine, amide, ester, ether or acid groups, and in particular in the form of hydroxyl, ester, ether or acid groups.

The oily phase generally comprises, in addition to the lipophilic UV-screening agent(s), at least one volatile or non-volatile hydrocarbon-based oil and/or one volatile and/or non-volatile silicone oil.

For the purposes of the invention, the term "volatile oil" means an oil that is capable of evaporating on contact with the skin or the keratin fibre in less than one hour, at room temperature and atmospheric pressure. The volatile oil(s) of the invention are volatile cosmetic oils which are liquid at room temperature and which have a non-zero vapour pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" means an oil that remains on the skin or the keratin fibre at room temperature and atmospheric pressure for at least several hours, and that especially has a vapour pressure of less than $10^{-3}$ mmHg (0.13 Pa).

Hydrocarbon-Based Oils

As non-volatile hydrocarbon-based oils that may be used according to the invention, mention may be made especially of:

(i) hydrocarbon-based oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheatgerm oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passionflower oil and musk rose oil; or also caprylic/capric acid triglycerides, such as those sold by Stéarineries Dubois or those sold under the names Miglyol 810®, 812® and 818® by Dynamit Nobel, (ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and squalane, and mixtures thereof;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms, on condition that R+R' is ≥10, for instance purcellin oil (cetearyl octanoate), isopropyl myristate, isopropyl palmitate, $C_{12}$-$C_{15}$ alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226® by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of Dub Dis by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by Enichem Augusta Industriale, and also di(linear $C_{14}$-$C_{15}$ alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CC® by the company Cognis;

(viii) fatty amides, such as isopropyl N-lauroyl sarcosinate, such as the product sold under the trade name Eldew SL 205® from Ajinomoto;

and mixtures thereof.

Among the non-volatile hydrocarbon-based oils that may be used according to the invention, preference will be given more particularly to glyceride triesters and in particular to caprylic/capric acid triglycerides, synthetic esters and in particular isononyl isononanoate, oleyl erucate, $C_{12}$-$C_{15}$ alkyl benzoate, 2-ethylphenyl benzoate and fatty alcohols, in particular octyldodecanol.

As volatile hydrocarbon-based oils that may be used according to the invention, mention may be made especially of hydrocarbon-based oils having from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isodecane or isohexadecane, the oils sold under the Isopar or Permethyl trade names, branched $C_8$-$C_{16}$ esters, isohexyl neopentanoate, and mixtures thereof.

Mention may also be made of the alkanes described in the Cognis patent applications WO 2007/068 371 or WO 2008/155 059 (mixtures of distinct alkanes differing by at least one carbon). These alkanes are obtained from fatty alcohols, which are themselves obtained from coconut or palm oil. Mention may be made of the mixtures of n-undecane ($C_{11}$) and n-tridecane ($C_{13}$) obtained in Examples 1 and 2 of patent application WO 2008/155 059 from the company Cognis. Mention may also be made of n-dodecane ($C_{12}$) and n-tetradecane ($C_{14}$), sold by Sasol under the respective references Parafol 12-97® and Parafol 14-97®, and also mixtures thereof.

Other volatile hydrocarbon-based oils, for instance petroleum distillates, especially those sold under the name Shell Solt® by the company Shell, may also be used.

According to one embodiment, the volatile solvent is chosen from volatile hydrocarbon-based oils containing from 8 to 16 carbon atoms, and mixtures thereof.

b) Silicone Oils

The non-volatile silicone oils may be chosen in particular from non-volatile polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

Examples of volatile silicone oils that may be mentioned include volatile linear or cyclic silicone oils, especially those with a viscosity≤8 centistokes ($8 \times 10^{-6}$ m$^2$/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Mention may also be made of the volatile linear alkyltrisiloxane oils of general formula (I):

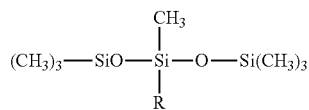

in which R represents an alkyl group comprising from 2 to 4 carbon atoms, one or more hydrogen atoms of which may be replaced with a fluorine or chlorine atom.

Among the oils of general formula (I), mention may be made of:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is, respectively, a butyl group, a propyl group or an ethyl group.

Fluoro Oils

Use may also be made of volatile fluoro oils, such as nonafluoromethoxybutane, decafluoropentane, tetradecafluorohexane, dodecafluoropentane, and mixtures thereof.

An oily phase according to the invention may also comprise other fatty substances, mixed with or dissolved in the oil.

Another fatty substance that may be present in the oily phase may be, for example:
  a fatty acid chosen from fatty acids comprising from 8 to 30 carbon atoms, such as stearic acid, lauric acid, palmitic acid and oleic acid;
  a wax chosen from waxes such as lanolin, beeswax, carnauba or candelilla wax, paraffin waxes, lignite waxes, microcrystalline waxes, ceresin or ozokerite, or synthetic waxes, such as polyethylene waxes or Fischer-Tropsch waxes;
  a gum chosen from silicone gums (dimethiconol);
  a pasty compound, such as polymeric or non-polymeric silicone compounds, esters of a glycerol oligomer, arachidyl propionate, fatty acid triglycerides and derivatives thereof;
  and mixtures thereof.

Preferentially, the overall oily phase, including all the lipophilic substances of the composition capable of being dissolved in this same phase, represents from 5% to 95% by weight and preferentially from 10% to 80% by weight, relative to the total weight of the composition.

Aqueous Phase

The compositions according to the invention may also comprise at least one aqueous phase.

The aqueous phase contains water and optionally other water-soluble or water-miscible organic solvents.

An aqueous phase that is suitable for use in the invention may comprise, for example, a water chosen from a natural spring water, such as water from La Roche-Posay, water from Vittel or waters from Vichy, or a floral water.

The water-soluble or water-miscible solvents that are suitable for use in the invention comprise short-chain monoalcohols, for example $C_1$-$C_4$ monoalcohols, such as ethanol or isopropanol; diols or polyols, such as ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether, glycerol and sorbitol, and mixtures thereof.

According to a preferred embodiment, use may more particularly be made of ethanol, propylene glycol, glycerol, and mixtures thereof.

According to a particular form of the invention, the overall aqueous phase, including all the hydrophilic substances of the composition capable of being dissolved in this same phase, represents from 5% to 95% by weight and preferably from 10% to 80% by weight, relative to the total weight of the composition.

Additives

The compositions according to the invention may also contain in free form one or more additional UV-screening agents chosen from organic UV-screening agents and/or one or more mineral screening agents with a mean elementary size of less than 0.1 µm such as those present in the composite UV-screening agents and described previously.

The compositions in accordance with the present invention may also comprise conventional cosmetic adjuvants chosen in particular from organic solvents, ionic or nonionic thickeners, softeners, humectants, opacifiers, stabilizers, emollients, silicones, antifoams, fragrances, preserving agents, anionic, cationic, nonionic, zwitterionic or amphoteric surfactants, active agents, fillers, polymers, propellants, basifying or acidifying agents or any other ingredient commonly used in the cosmetic and/or dermatological field.

Mention may be made, among organic solvents, of alcohols other than $C_1$-$C_4$ monoalkanols as defined above and in particular short-chain $C_2$-$C_8$ polyols, such as glycerol or diols, such as caprylyl glycol, 1,2-pentanediol, propanediol, butanediol, glycols and glycol ethers, such as ethylene glycol, propylene glycol, butylene glycol, dipropylene glycol or diethylene glycol.

Mention may be made, as thickeners, of carboxyvinyl polymers, such as the Carbopols® (Carbomers) and the Pemulens, such as Pemulen TR1® and Pemulen TR2® (acrylate/$C_{10}$-$C_{30}$ alkyl acrylate copolymer); polyacrylamides, for instance the crosslinked copolymers sold under the names Sepigel 305® (CTFA name: polyacrylamide/$C_{13-14}$ isoparaffin/laureth 7) or Simulgel 600 (CTFA name: acrylamide/sodium acryloyldimethyl taurate copolymer/isohexadecane/polysorbate 80) by the company SEPPIC; 2-acrylamido-2-methylpropanesulfonic acid polymers and copolymers, optionally crosslinked and/or neutralized, such as the poly(2-acrylamido-2-methylpropanesulfonic acid) sold by the company Hoechst under the trade name Hostacerin AMPS® (CTFA name: ammonium polyacryloyldimethyl taurate) or Simulgel 800®, sold by the company SEPPIC (CTFA name: sodium polyacryloyldimethyl taurate/polysorbate 80/sorbitan oleate); copolymers of 2-acrylamido-2-methylpropanesulfonic acid and of hydroxyethyl acrylate, such as Simulgel NS® and Sepinov EMT 10®, sold by the company SEPPIC; cellulose derivatives, such as hydroxyethylcellulose; polysaccharides and in particular gums, such as xanthan gum; water-soluble or water-dispersible silicone derivatives, such as acrylic silicones, polyether silicones and cationic silicones, and mixtures thereof.

Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

Among the basifying agents, examples that may be mentioned include aqueous ammonia, alkali metal carbonates, alkanolamines, such as mono-, di- and triethanolamines and derivatives thereof, sodium hydroxide or potassium hydroxide.

Preferably, the cosmetic composition comprises one or more basifying agents selected from alkanolamines, in particular triethanolamine, and sodium hydroxide.

In the case of a direct emulsion, the pH of the composition in accordance with the invention is generally between 3 and 12 approximately, preferably between 5 and 11 approximately and even more particularly from 6 to 8.5.

Among the active agents for caring for keratin materials such as the skin, the lips, the scalp, the hair, the eyelashes or the nails, examples that may be mentioned include:
vitamins and derivatives or precursors thereof, alone or as mixtures;
antioxidants;
free-radical scavengers;
antipollution agents;
self-tanning agents;
antiglycation agents;
calmatives;
deodorants;
essential oils;
NO-synthase inhibitors;
agents for stimulating the synthesis of dermal or epidermal macromolecules and/or for preventing their degradation;
agents for stimulating fibroblast proliferation;
agents for stimulating keratinocyte proliferation;
muscle relaxants;
refreshing agents;
tensioning agents;
matting agents;
depigmenting agents;
propigmenting agents;
keratolytic agents;
desquamating agents;
moisturizers;
antiinflammatory agents;
antimicrobial agents;
slimming agents;
agents acting on the energy metabolism of cells;
insect repellents;
substance P or CGRP antagonists;
hair-loss counteractants;
antiwrinkle agents;
antiageing agents.

A person skilled in the art will select the said active agent(s) as a function of the effect desired on the skin, the hair, the eyelashes, the eyebrows and the nails.

Needless to say, a person skilled in the art will take care to choose the abovementioned optional additional compound(s) and/or the amounts thereof so that the advantageous properties intrinsically attached to the compositions in accordance with the invention are not, or not substantially, detrimentally affected by the envisaged addition(s).

Galenical Forms

The compositions according to the invention may be prepared according to the techniques that are well known to those skilled in the art. They may in particular be in the form of a gel, a simple or complex emulsion (O/W, W/O, O/W/O or W/O/W), such as a cream, a milk or a cream gel.

They may also be in anhydrous form, for instance in the form of an oil. The term "anhydrous composition" means a composition containing less than 1% by weight of water, or even less than 0.5% of water, and especially free of water, the water not being added during the preparation of the composition but corresponding to the residual water provided by the mixed ingredients.

They may optionally be packaged in aerosol form and may be in the form of a mousse or a spray.

In the case of compositions in the form of oil-in-water or water-in-oil emulsions, the emulsification processes that may be used are of the paddle or impeller, rotor-stator and HPH type.

In order to obtain stable emulsions with a low content of polymer (oil/polymer ratio>25), it is possible to prepare the dispersion in concentrated phase and then to dilute the dispersion with the remainder of the aqueous phase.

It is also possible, by means of an HPH (between 50 and 800 bar), to obtain stable dispersions with drop sizes that may be as low as 100 nm.

The emulsions generally contain at least one emulsifier chosen from amphoteric, anionic, cationic and nonionic emulsifiers, used alone or as a mixture. The emulsifiers are appropriately chosen according to the emulsion to be obtained (W/O or O/W).

The compositions according to the invention are preferably in the form of an oil-in-water or water-in-oil emulsion. The emulsifying surfactants are appropriately chosen according to the emulsion to be obtained.

Non-limiting examples of W/O emulsifying surfactants suitable for water-in-oil emulsions are especially given in the publication entitled *McCutcheon's Emulsifiers & Detergents,* 1998, International Edition, MC Publishing Company, in the chapter entitled HLB Index.

Examples of W/O emulsifying surfactants that may be mentioned include alkyl esters or ethers of sorbitan, of glycerol, of polyol or of sugars; silicone surfactants, for instance dimethicone copolyols, such as the mixture of cyclomethicone and of dimethicone copolyol, sold under the name DC 5225 C® by the company Dow Corning, and alkyldimethicone copolyols such as laurylmethicone copolyol sold under the name Dow Corning 5200 Formulation Aid by the company Dow Corning; cetyldimethicone copolyol, such as the product sold under the name Abil EM 90R® by the company Goldschmidt, and the mixture of cetyldimethicone copolyol, of polyglyceryl isostearate (4 mol) and of hexyl laurate, sold under the name Abil WE O9® by the company Goldschmidt. One or more coemulsifiers may also be added thereto, which coemulsifiers may be chosen advantageously from the group comprising polyol alkyl esters.

Mention may also be made of non-silicone emulsifying surfactants, in particular alkyl esters or ethers of sorbitan, of glycerol, of polyol or of sugars.

Polyol alkyl esters that may especially be mentioned include polyethylene glycol esters, for instance PEG-30 dipolyhydroxystearate, such as the product sold under the name Arlacel P135® by the company ICI.

Examples of glycerol and/or sorbitan esters that may be mentioned include polyglyceryl isostearate, such as the product sold under the name Isolan GI 34® by the company Goldschmidt; sorbitan isostearate, such as the product sold under the name Arlacel 987® by the company ICI; sorbitan glyceryl isostearate, such as the product sold under the name Arlacel 986® by the company ICI, and mixtures thereof.

For the O/W emulsions, examples of nonionic emulsifying surfactants that may be mentioned include polyoxyalkylenated (more particularly polyoxyethylenated and/or polyoxypropylenated) esters of fatty acids and of glycerol; oxyalkylenated esters of fatty acids and of sorbitan; polyoxyalkylenated (in particular polyoxyethylenated and/or polyoxypropylenated) esters of fatty acids, optionally in combination with an ester of fatty acid and of glycerol, such as the PEG-100 Stearate/Glyceryl Stearate mixture sold, for example, by the company ICI under the name Arlacel 165; oxyalkylenated (oxyethylenated and/or oxypropylenated) ethers of fatty alcohols; esters of sugars, such as sucrose stearate; or ethers of fatty alcohol and of sugar, in particular alkyl polyglucosides (APGs), such as decyl glucoside and lauryl glucoside, sold, for example, by the company Henkel under the respective names Plantaren 2000® and Plantaren 1200®, cetostearyl glucoside, optionally as a mixture with cetostearyl alcohol, sold, for example, under the name Montanov 68® by the company SEPPIC, under the name Tegocare CG90® by the company Goldschmidt and under the name Emulgade KE3302® by the company Henkel, and arachidyl glucoside, for example in the form of the mixture of arachidyl and behenyl alcohols and of arachidyl glucoside sold under the name Montanov 202® by the company SEPPIC. According to a particular embodiment of the invention, the mixture of the alkylpolyglucoside as defined above with the corresponding fatty alcohol may be in the form of a self-emulsifying composition, for example as described in document WO-A-92/06778.

According to a particularly preferred form, the compositions are in the water-in-oil form.

When it is an emulsion, the aqueous phase of this emulsion may comprise a nonionic vesicular dispersion prepared according to known processes (Bangham, Standish and Watkins, J. Mol. Biol. 13, 238 (1965), FR 2 315 991 and FR 2 416 008).

The compositions according to the invention find their application in a large number of treatments, especially cosmetic treatments, of the skin, the lips and the hair, including the scalp, especially for protecting and/or caring for the skin, the lips and/or the hair, and/or for making up the skin and/or the lips.

Another subject of the present invention consists of the use of the compositions according to the invention as defined above for the manufacture of products for cosmetic treatment of the skin, the lips, the nails, the hair, the eyelashes, the eyebrows and/or the scalp, especially care products, antisun products and makeup products.

The cosmetic compositions according to the invention may be used, for example, as makeup products.

Another subject of the present invention consists of a non-therapeutic cosmetic process for caring for and/or making up a keratin material, which consists in applying, to the surface of the said keratin material, at least one composition according to the invention as defined above.

The cosmetic compositions according to the invention may be used, for example, as care products and/or antisun products for the face and/or the body with a liquid to semi-liquid consistency, such as milks, more or less smooth creams, cream gels or pastes. They may optionally be packaged in aerosol form and may be in the form of a mousse or a spray.

The compositions according to the invention in the form of vaporizable fluid lotions in accordance with the invention are applied to the skin or the hair in the form of fine particles by means of pressurization devices. The devices in accordance with the invention are well known to those skilled in the art and comprise non-aerosol pumps or "atomizers", aerosol containers comprising a propellant and aerosol pumps using compressed air as propellant. These devices are described in U.S. Pat. No. 4,077,441 and U.S. Pat. No. 4,850,517.

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

Assembly

According to another aspect, the invention also relates to a cosmetic assembly comprising:

i) a container delimiting one or more compartment(s), the said container being closed by a closing member and optionally not being leaktight; and ii) a makeup and/or care composition in accordance with the invention placed inside the said compartment(s).

The container may be, for example, in the form of a jar or a box.

The closing member may be in the form of a lid comprising a cap mounted so as to be able to move by translation or by pivoting relative to the container housing the said makeup and/or care composition(s).

The examples that follow serve to illustrate the invention without, however, being limiting in nature. In these examples, the amounts of the composition ingredients are given as weight percentages relative to the total weight of the composition.

EXAMPLES

Examples 1 to 2

The components indicated in Table 1 were placed in a hybridizer equipped with a high-speed rotor fitted with a plurality in a dry chamber in a Nara Machinery® device, to obtain a composite material.

The components indicated in Table 1 were mixed in the indicated proportions in a plastic bag shaken by hand for a short period. The mixture was placed in the hybridizer machine and the rotor speed was set at 8000 rpm (linear velocity of 100 m/s) for 3 minutes.

The UV absorbance was evaluated for each composite UV-screening agent 1 to 4 with a V-500 model UV/visible spectrophotometer (Jasco, Japan) under the following conditions:

A solvent was prepared by mixing isododecane and polyhydroxystearic acid such that the polyhydroxystearic acid concentration was 3% by weight.

Each composite UV-screening agent was dispersed in the said solvent thus obtained by ultrasonication for 1 minute to obtain a sample suspension at 0.1% by weight in the said solvent. If the agglomerates are still present, the ultrasonication treatment is repeated.

The sample thus obtained was placed in a quartz cell with a light path length of 2 mm. The absorbance of each sample was measured in the wavelength range from 280 to 400 nm with a V-500 model UV/visible spectrophotometer (Jasco, Japan). The results are given in Table 1 below.

TABLE 1

| Composite UV-screening agent | Core particle A | Core particle B | UV-screening agent | UV absorbance |
|---|---|---|---|---|
| Mean size | 0.35 µm | 6 µm | 0.015 µm | |
| Material | Styrene/Acrylate Copolymer [1] | Polymethyl methacrylate [2] | TiO$_2$ [3] | |
| Example 1 | 35 | 15 | 50 | 129 |
| Example 2 | 50 | 20 | 30 | 103 |

[1] Styrene/Acrylate Copolymer: Sunspheres ® - Röhm & Haas
[2] PMMA MR-7GC ® - Soken
[3] TiO$_2$: MT-100 TV ® - Tayca Examples 3 to 7

The water-in-oil emulsions 3 to 7 were prepared according to the following protocol:

The oily phase A$_1$ was prepared by mixing the starting materials with mechanical stirring at 70-80° C. The phases A$_2$, A$_3$ and A$_4$ were added after cooling of A$_1$ to about 60-65° C. The aqueous phase (B$_1$, B$_2$, B$_3$) was prepared by mixing the starting materials with mechanical stirring at 65-70° C. The solutions obtained were macroscopically homogeneous. The emulsion was prepared by slow introduction of the aqueous phase into the oily phase with stirring using a Moritz homogenizer at a stirring speed of 4500 rpm for 10 minutes. The oily phase C was added to the emulsion obtained with gentle stirring. The emulsion obtained was cooled to room temperature with slow stirring and phase D was then added. The final emulsion was characterized by drops of between 1 µm and 10 µm in size.

These compositions were evaluated according to the following properties:

Sedimentation of the particles

Aggregation of the particles

The examples were compared with a particle content equal to 5% by weight relative to the total weight of the composition.

Evaluation

The formulae were first centrifuged at 2000 rpm for 30 minutes.

The sedimentation of the particles was evaluated visually.

The aggregation of the particles was evaluated by optical microscopy observation with a ×20 objective lens.

The sedimentation and aggregation of the particles were graded + or −

+ sedimentation observed and aggregation observed by microscope

− absence of sedimentation and absence of aggregation observed by microscope

| Phase | INCI Name | Ex. 3 | Ex. 4 (*) |
|---|---|---|---|
| A1 | PEG-30 dipolyhydroxystearate | 2.00 | 2.00 |
| | Synthetic wax | 1.00 | 1.00 |
| | Octocrylene | 2.50 | 2.50 |
| | Butylmethoxydibenzoylmethane | 3.00 | 3.00 |
| | Ethylhexyl triazone | 1.00 | 1.00 |

| Phase | INCI Name | Ex. 3 | Ex. 4 (*) |
|---|---|---|---|
| | Bis(ethylhexyloxyphenol)methoxyphenyltriazine | 2.00 | 2.00 |
| | Drometrizole trisiloxane | 0.50 | 0.50 |
| | Ethylhexyl salicylate | 5.00 | 5.00 |
| | C12-15 Alkyl benzoate | 7.50 | 7.50 |
| | Caprylic/capric triglyceride | 5.00 | 5.00 |
| | Caprylyl glycol | 0.50 | 0.50 |
| | Silica silylate (VM 2270 ®) | 2.00 | − |
| A2 | Lauryl PEG/PPG-18/18 methicone (and) dodecene (and) poloxamer 407 | 2.00 | 2.00 |
| | Cyclohexasiloxane | 6.00 | 6.00 |
| A3 | Composite screening agent according to Example 1 (mean elementary size > 0.1 µm) | 5 | 5 |
| | Tocopherol | 0.20 | 0.20 |
| | Silica | 0.10 | 0.10 |
| B1 | Water | 30.11 | 32.11 |
| | Ammonium polyacryloyldimethyl taurate | 0.50 | 0.50 |
| B2 | Glycerol | 2.00 | 2.00 |
| | Propylene glycol | 4.00 | 4.00 |
| | Pentasodium ethylenediamine tetramethylene phosphonate | 0.30 | 0.30 |
| B3 | Terephthalylidenedicamphorsulfonic acid | 4.50 | 4.50 |
| | Triethanolamine | 0.78 | 0.78 |
| C | Cyclopentasiloxane (and) disteardimonium hectorite (and) denatured alcohol | 2.00 | 2.00 |
| | Isododecane | 4.50 | 4.50 |
| D | Denatured alcohol | 6.00 | 6.00 |
| | Aggregation and sedimentation after 2000 rpm for 30 minutes | − | + |

(*) outside the invention

It was observed that, in formula 4 outside the invention, the composite particles based on TiO$_2$ screening out UV radiation, with a mean size of greater than 0.1 µm, sediment in the absence of hydrophobic silica aerogel particles.

However, by adding silica aerogel particles in formula 3 according to the invention, it was found that the dispersion of the particles of the composites based on TiO$_2$ was improved.

| Phase | INCI Name | Ex. 5 (*) | Ex. 6 |
|---|---|---|---|
| A1 | PEG-30 dipolyhydroxystearate | 2.00 | 2.00 |
| | Synthetic wax | 1.00 | 1.00 |
| | Octocrylene | 2.50 | 2.50 |
| | Butylmethoxydibenzoylmethane | 3.00 | 3.00 |
| | Ethylhexyl triazone | 1.00 | 1.00 |
| | Bis(ethylhexyloxyphenol)methoxyphenyltriazine | 2.00 | 2.00 |
| | Drometrizole trisiloxane | 0.50 | 0.50 |
| | Ethylhexyl salicylate | 5.00 | 5.00 |
| | C12-15 Alkyl benzoate | 7.50 | 7.50 |
| | Caprylic/capric triglyceride | 5.00 | 5.00 |
| | Caprylyl glycol | 0.50 | 0.50 |
| | Dextrin palmitate (Rheopearl KL2 - OR) | − | 1.00 |
| | Silica silylate (Aerogel) | − | 1.00 |
| A2 | Lauryl PEG/PPG-18/18 methicone (and) dodecene (and) poloxamer 407 | 2.00 | 2.00 |
| | Cyclohexasiloxane | 6.00 | 6.00 |
| A3 | Tocopherol | 0.20 | 0.20 |
| | Composite screening agent Silica and titanium dioxide (Sunjin TIN 50 ®) (mean size: 2-7 µm) | 5.00 | 5.00 |
| | Silica | 0.10 | 0.10 |
| B1 | Water | 32.11 | 30.11 |
| | Ammonium polyacryloyldimethyl taurate | 0.50 | 0.50 |
| B2 | Glycerol | 2.00 | 2.00 |
| | Propylene glycol | 4.00 | 4.00 |
| | Pentasodium ethylenediamine tetramethylene phosphonate | 0.30 | 0.30 |

-continued

| Phase | INCI Name | Ex. 5 (*) | Ex. 6 |
|---|---|---|---|
| B3 | Terephthalylidenedicamphorsulfonic acid | 4.50 | 4.50 |
|  | Triethanolamine | 0.78 | 0.78 |
| C | Cyclopentasiloxane (and) disteardimonium hectorite (and) denatured alcohol | 2.00 | 2.00 |
|  | Isododecane | 4.50 | 4.50 |
| D | Denatured alcohol | 6.00 | 6.00 |
|  | Aggregation and sedimentation after 2000 rpm for 30 minutes | + | − |

(*) outside the invention

It was observed that, in formula 5, the composite particles based on TiO₂ screening out UV radiation, with a mean size of greater than 0.1 μm, sediment in the absence of hydrophobic silica aerogel particles.

However, by adding silica aerogel particles in formula 6 according to the invention, it was found that the dispersibility of the particles of the composites based on TiO₂ was improved.

Examples 3 and 7

Protocol for evaluating the sensory effect after application to the skin

The sensory effect after application of the formula to the skin is evaluated by applying the formula to a forearm at a rate of 2 mg/cm², waiting for a drying time equal to 2 minutes and then assessing the friction force felt between the fingers and the surface of the forearm. The sensory smoothness was graded + or −.

+ smooth
− coarse

| Phase | INCI Name | Ex. 3 | Ex. 7 |
|---|---|---|---|
| A1 | PEG-30 dipolyhydroxystearate | 2.00 | 2.00 |
|  | Synthetic wax | 1.00 | 1.00 |
|  | Octocrylene | 2.50 | 2.50 |
|  | Butylmethoxydibenzoylmethane | 3.00 | 3.00 |
|  | Ethylhexyl triazone | 1.00 | 1.00 |
|  | Bis(ethylhexyloxyphenol)methoxyphenyltriazine | 2.00 | 2.00 |
|  | Drometrizole trisiloxane | 0.50 | 0.50 |
|  | Ethylhexyl salicylate | 5.00 | 5.00 |
|  | C12-15 Alkyl benzoate | 7.50 | 7.50 |
|  | Caprylic/capric triglyceride | 5.00 | 5.00 |
|  | Caprylyl glycol | 0.50 | 0.50 |
|  | Dextrin palmitate (Rheopearl KL2 - OR) | − | 1.00 |
|  | Silica silylate (VM 2270 ®) | 2.00 | 1.00 |
| A2 | Lauryl PEG/PPG-18/18 methicone (and) dodecene (and) poloxamer 407 | 2.00 | 2.00 |
|  | Cyclohexasiloxane | 6.00 | 6.00 |
| A3 | Composite screening agent according to Example 1 (mean elementary size > 0.1 μm) | 5.00 | 5.00 |
|  | Tocopherol | 0.20 | 0.20 |
|  | Silica | 0.10 | 0.10 |
| B1 | Water | 30.11 | 30.11 |
|  | Ammonium polyacryloyldimethyl taurate | 0.50 | 0.50 |
| B2 | Glycerol | 2.00 | 2.00 |
|  | Propylene glycol | 4.00 | 4.00 |
|  | Pentasodium ethylenediamine tetramethylene phosphonate | 0.30 | 0.30 |
| B3 | Terephthalylidenedicamphorsulfonic acid | 4.50 | 4.50 |
|  | Triethanolamine | 0.78 | 0.78 |
| C | Cyclopentasiloxane (and) disteardimonium hectorite (and) denatured alcohol | 2.00 | 2.00 |
|  | Isododecane | 4.50 | 4.50 |
| D | Denatured alcohol | 6.00 | 6.00 |
|  | Sensory result | − | + |

(*) outside the invention

By adding dextrin palmitate in formula 7 according to the invention, it was found that the sensory result was smoother and more pleasant.

The invention claimed is:

1. A composition comprising, in a cosmetically acceptable medium:
   a) composite particles with a mean size of greater than 0.1 μm, containing a matrix comprising
      i) at least one organic material and/or at least one mineral material and
      ii) at least titanium dioxide, optionally treated with at least one surface-treatment agent; and
   b) hydrophobic silica aerogel particles having a hydrophobic silica aerogel particles have a specific surface area per unit of mass ($S_M$) ranging from 600 to 1200 m²/g.

2. The composition according to claim 1, in which the hydrophobic silica aerogel particles have a specific surface area per unit of mass ($S_M$) ranging from 600 to 800 m²/g and a size, expressed as the volume-mean diameter (D[0.5]), of less than 1500 μm.

3. The composition according to claim 1, wherein the hydrophobic silica aerogel particles have at least one of the following conditions:
   a tapped density ρ ranging from 0.04 g/cm³ to 0.10 g/cm³;
   a specific surface area per unit of volume SV ranging from 5 to 60 m²/cm³;
   an oil-absorbing capacity, measured at the wet point, ranging from 5 to 18 ml/g.

4. The composition according to claim 1, wherein the hydrophobic silica aerogel particles are silica particles modified with trimethylsilyl groups.

5. The composition according to claim 1, wherein the composite particles are chosen from:
   (i) composite particles containing a matrix comprising an organic and/or mineral material, in which matrix particles of mineral UV-screening agent are included;
   (ii) composite particles containing a matrix comprising an organic and/or mineral material, which matrix is covered with at least one layer of mineral UV-screening agent which can be connected to the matrix by means of a binder;
   (iii) composite particles containing at least one mineral UV-screening agent covered with at least one layer of an organic and/or mineral material.

6. The composition according to claim 1, wherein the matrix of the composite particle contains a material or a mixture of materials chosen from:
   silica,
   talc,
   mica,
   alumina,
   an alumina/triethoxycaprylylsilane mixture,
   polymethyl methacrylate, copolymers of styrene and of (meth)acrylic acid or a ($C_1$-$C_{20}$)alkyl ester thereof,
polyamides,
and mixtures thereof.

7. The composition according to claim 1, wherein the composite particles comprise at least one core particle A with a mean size of greater than 0.1 µm and less than 1 µm; the surface of the said core being at least partially covered with at least one layer of at least one mineral UV-screening agent.

8. The composition according to claim 7 wherein the composite particles comprise:
   a) at least one core particle A with a mean size of greater than 0.1 µm and less than 1 µm; the surface of the said core being at least partially covered with at least one layer of titanium dioxide, and
   b) at least one core particle B with a mean size of at least 2 µm; the surface of the said core being at least partially covered with at least one layer of titanium dioxide.

9. The composition according to claim 7, wherein the composite particles comprise:
   a) at least one hollow spherical core particle A with a mean size of greater than 0.1 µm and less than 1 µm, comprising at least one copolymer of styrene and of (meth)acrylic acid or a ($C_1$-$C_{20}$)alkyl ester thereof; the surface of the said core A being at least partially covered with at least one layer of titanium dioxide,
   b) at least one spherical core particle B with a mean size of at least 2 µm, comprising at least one poly(meth)acrylate; the surface of the said core B being at least partially covered with at least one layer of titanium dioxide.

10. The composition according to claim 7, wherein the composite particles are prepared according to a mechano-chemical melting process.

11. The composition according to claim 1, wherein it also comprises at least one dextrin ester.

12. The composition according to claim 1, wherein it is in the form of a gel, a simple or complex emulsion or in anhydrous form.

13. A cosmetic process for caring for and/or making up human keratin materials comprising at least the application, to the surface of the keratin material, of a composition as defined according to claim 1.

14. A non-therapeutic cosmetic process for limiting the darkening of the skin and/or improving the colour and/or uniformity of the complexion, comprising the application, to the surface of the keratin material, of a composition as defined according to claim 1.

15. A non-therapeutic cosmetic process for preventing and/or treating the signs of ageing of a keratin material, comprising the application, to the surface of the keratin material, of a composition as defined according to claim 1.

16. The composition according to claim 3, in which the hydrophobic silica aerogel particles have a specific surface area per unit of mass ($S_M$) ranging from 600 to 800 $m^2/g$ and a size, expressed as the volume-mean diameter (D[0.5]), ranging from 1 to 30 µm.

17. The composition according to claim 1 wherein the hydrophobic silica aerogel particles have all of the following conditions:
   a tapped density p ranging from 0.04 $g/cm^3$ to 0.10 $g/cm^3$;
   a specific surface area per unit of volume SV ranging from 5 to 60 $m^2/cm^3$;
   an oil-absorbing capacity, measured at the wet point, ranging from 5 to 18 ml/g.

18. The composition according to claim 2 wherein the hydrophobic silica aerogel particles have at least one of the following conditions:
   a tapped density p ranging from 0.04 $g/cm^3$ to 0.10 $g/cm^3$;
   a specific surface area per unit of volume SV ranging from 5 to 60 $m^2/cm^3$;
   an oil-absorbing capacity, measured at the wet point, ranging from 5 to 18 ml/g.

19. The composition according to claim 2, wherein the hydrophobic silica aerogel particles are silica particles modified with trimethylsilyl groups.

20. The composition according to claim 3, wherein the hydrophobic silica aerogel particles are silica particles modified with trimethylsilyl groups.

* * * * *